United States Patent [19]

Katsuyama et al.

[11] Patent Number: 5,698,564
[45] Date of Patent: Dec. 16, 1997

[54] DIPHENYL DISULFIDE COMPOUNDS

[75] Inventors: Koichi Katsuyama; Masato Ariga, both of Ohimachi; Yukio Saito, Tokyo; Shigeo Hatanaka; Toshihiro Takahashi, both of Ohimachi, all of Japan

[73] Assignee: Nisshin Flour Milling Co., Ltd., Tokyo, Japan

[21] Appl. No.: 576,681

[22] Filed: Dec. 21, 1995

[30] Foreign Application Priority Data

Dec. 16, 1994 [JP] Japan ................... 6-322072

[51] Int. Cl.$^6$ .............. C07D 231/54; C07D 239/02; A61K 31/495
[52] U.S. Cl. .............. 514/275; 514/275; 544/331; 544/332; 544/296; 548/310.7
[58] Field of Search ................... 544/332, 331, 544/296; 548/310.7; 514/275, 394

[56] References Cited

FOREIGN PATENT DOCUMENTS

| | | |
|---|---|---|
| 0 611 757 A1 | 2/1994 | European Pat. Off. |
| WO92/05164 | 4/1992 | WIPO |

OTHER PUBLICATIONS

Dusemund J., "Reactions of 1-Aminothioxanthone-6,6-Dioxides with Formamide.", Chem. Abs., vol. 83 (1975), #79178, p. 658.

Berge et al., Wiss. Z (1983), 32, 78-9.

Leopold Horner, et al., Phosphorus and Sulfur and The Related Elements. "Phosphororganische Verbindungen 117$^1$, Eine Neue Methode Zum Nachweis Der Funktionellen Gruppen: OH, NH$_2$ Und Sh Durch Auslösung Von Fluoreszenz", 1987, vol. 32, pp. 91–97.

*Primary Examiner*—Mukund J. Shah
*Assistant Examiner*—Tamthom T. Ngo
*Attorney, Agent, or Firm*—Oblon, Spivak, McClelland, Maier & Neustadt, P.C.

[57] ABSTRACT

Diphenyl disulfide compounds having an inhibiting activity against the production of Interleukin-1β (IL-1β) or the release of Tumor Necrosis Factorα (TNFα), which are useful in the treatment or prophylaxis of the diseases such as chronic rheumatism and sepsis are described.

6 Claims, No Drawings

DIPHENYL DISULFIDE COMPOUNDS

FIELD OF THE INVENTION

This invention relates to novel diphenyl disulfide compounds having the activities to inhibit the production of Interleukin-1β (IL-1β) and the release of Tumor Necrosis Factorα (TNFα).

BACKGROUND OF THE INVENTION

IL-1β is a protein produced mainly from immunocompetent cells such as macrophages and neutrophils, which is an important factor for immune response. Also, it is known to be a factor playing a central role in the inflammatory process or a factor participating in many vital reactions such as hematopoiesis, internal secretion and nervous system.

For instance, there has been recently clarified the relationship between IL-1β and inflammatory diseases such as chronic rheumatism. IL-1β was detected in the synovial membrane of patients suffering from chronic rheumatism. It was reported that the IL-1β level in synovial fluid correlated with observations on the local inflammation.

2,2'-Diamino-diphenyl disulfide and 4-amino-2'-nitrodiphenyl disulfide are known as one of the starting materials for synthesis of organic compounds, respectively in WO 92/05164 and "Phosphorus and Sulfur", 1987, vol. 32, pp. 91–97. However, there is no reference to their pharmaceutical uses.

Steroidal agents and non-steroidal anti-inflammatory agents have been used for the treatment of inflammatory diseases such as chronic rheumatism. Steroidal agents can achieve remarkable improvement in various symptoms of inflammatory diseases, but they present the problems that drug tolerance may be developed by administration over a prolonged period of time and that side-effects, sometimes serious, such as gastrointestinal disturbance, dermatopathy and nephritis may be caused. Non-steroidal agents can temporarily inhibit inflammatory symptoms, but they cannot radically cure inflammatory diseases.

SUMMARY OF THE INVENTION

Under these circumstances, we have found that new diphenyl disulfide compounds have potent activities to inhibit the production of IL-1β and the release or liberation of TNFα, which are useful as a therapeutic agent for chronic rheumatism and sepsis.

The present invention provides a new diphenyl disulfide compound of formula (I) and the pharmacologically acceptable salts thereof.

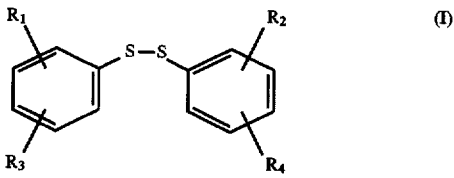

(I)

wherein $R_1$ is a 5- or 6-membered heterocyclic group containing two nitrogen atoms as a hetero atom; said heterocyclic group condensed with a phenyl ring; an amino group; or an amino group which is mono-substituted by a 5- or 6-membered heterocyclic group containing two nitrogen atoms as a hetero atom or by said heterocyclic group condensed with a phenyl ring; $R_2$ is a 5- or 6-membered heterocyclic group having two nitrogen atoms as a hetero atom; said heterocyclic group condensed with a phenyl ring; an amino group; an amino group which is mono-substituted by a 5- or 6-membered heterocyclic group containing two nitrogen atoms as a hetero atom or by said heterocyclic group condensed with a phenyl ring; or a nitro group; and $R_3$ and $R_4$ may be the same or different and each is a hydrogen atom; an alkyl group of 1–4 carbon atoms; an alkoxy group of 1–4 carbon atoms; an amino group; or a nitro group; provided that, when $R_1$ is an amino group, $R_2$ is not an amino or nitro group.

The present invention also provides a pharmaceutical composition which comprises as an active ingredient the diphenyl disulfide compound of formula (I) or a pharmacologically acceptable salt thereof.

The present invention also includes a pharmaceutical composition having the activities to inhibit the production of IL-1β and the release of TNFα, which is useful as a therapeutic agent for chronic rheumatism and sepsis.

DETAILED DESCRIPTION OF THE INVENTION

The groups $R_1$ and $R_3$ are substituted on one phenyl ring in the compound of formula (I), while the groups $R_2$ and $R_4$ are substituted on the other phenyl ring. These groups $R_1$ to $R_4$ are substituted at any position in each phenyl ring, but preferably substituted at the 2- and 4-positions.

Examples of the 5- or 6-membered heterocyclic groups as defined for $R_1$ and $R_2$ include heteroaromatic groups such as imidazolyl, pyrazolyl, pyrazinyl, pyrimidinyl and pyridazinyl groups; and non-aromatic heterocyclic groups such as imidazolinyl, pyrazolinyl, imidazolidinyl, pyrazolidinyl, piperazinyl, hexahydropyrimidinyl and hexahydropyridazinyl groups. Examples of the 5- or 6-membered heterocyclic groups condensed with a phenyl ring as defined for $R_1$ and $R_2$ include condensed heteroaromatic groups such as benzimidazoyl, cinnolinyl, purinyl, indazolyl, quinoxalinyl and quinazolinyl groups; and non-aromatic condensed heterocyclic groups such as benzpyrazolidinyl, benzimidazolidinyl and benzpiperazinyl groups.

Examples of the $C_1$–$C_4$ alkyl groups as defined for $R_3$ and $R_4$ include straight or branched alkyl groups such as methyl, ethyl, n-propyl, isopropyl, n-butyl, isobutyl and tert-butyl groups.

Examples of the $C_1$–$C_4$ alkoxy groups as defined for $R_3$ and $R_4$ include those derived from straight or branched alkyl groups of 1–4 carbon atoms, e.g. methoxy, ethoxy and n-propoxy groups.

The compounds of formula (I) can be synthesized according to various processes. One of these processes comprises reacting a di(aminophenyl)disulfide compound of formula (II)

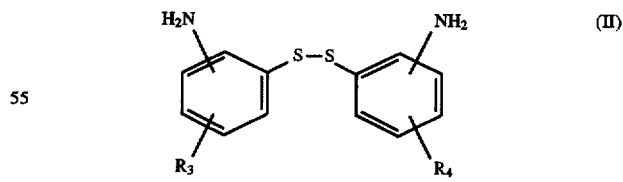

(II)

wherein $R_3$ and $R_4$ are as defined above, with a halide of the formula R'Hal or a mixed halide wherein R' is a 5- or 6-membered heterocyclic group containing two nitrogen atoms as a hetero atom or said heterocyclic group condensed with a phenyl ring and Hal is a halogen atom, by which one or both of the amino groups in the compound of formula (II) is mono-substituted by said heterocyclic group.

This reaction is carried out by using 0.5–4 moles of the compound of the formula R'Hal per mole of the compound of formula (II). When the halide is used in lower mole, the product may be predominantly prepared wherein one of the amino groups is mono-substituted by the heterocyclic group. When the halide is used in higher mole, the product may be predominantly prepared wherein both of the amino groups are mono-substituted by the heterocyclic groups.

This reaction is carried out in an inert organic solvent, preferably in the presence of an acid binding agent such as an inorganic base, e.g. sodium hydroxide, potassium hydroxide, sodium carbonate and potassium carbonate and an organic base, e.g. pyridine, picoline and lutidine. As the inert organic solvent may be used any organic solvents giving no adverse effect on the reaction, which include an alcohol such as methanol, ethanol, propanol and butanol; a hydrocarbon such as acetone, a ketone, e.g. methyl ethyl ketone; cyclohexane, benzene and toluene; and an ether such as ether and tetrahydrofuran. The reaction is carried out at a temperature ranging from ordinary temperature to a boiling point of the solvent used.

Alternatively, the compound of formula (I) can be prepared by reacting a mercapto compound of formula (III) or a reactive derivative thereof

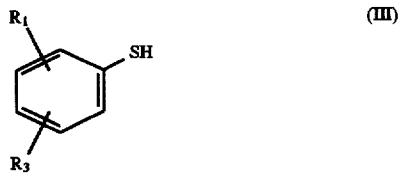

wherein $R_1$ and $R_3$ are as defined above, with a mercapto compound of formula (IV) or a reactive derivative thereof

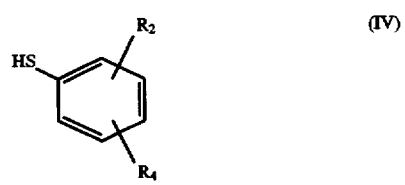

wherein $R_2$ and $R_4$ are as defined above to form the disulfide bond.

In this instance, the reaction of two mercapto compounds may be carried out by using a suitable oxidizing agent, e.g. hydrogen peroxide, iodine, bromine, a hypoiodite and sulfuryl chloride. Alternatively, this reaction can be performed by converting the mercapto group of either the compound (III) or the compound (IV) to the corresponding mercury salt, zinc salt or lead salt and another mercapto group to the corresponding sulfenyl chloride, followed by reacting both compounds. This reaction may be preferably conducted in an inert organic solvent as recited above. The reaction is carried out at a temperature ranging from ordinary temperature to a boiling point of the solvent used.

Illustrative examples of the compounds of formula (I) are shown by way of the following chemical structures:

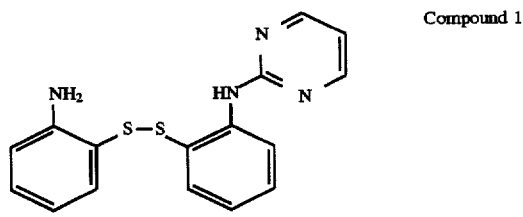

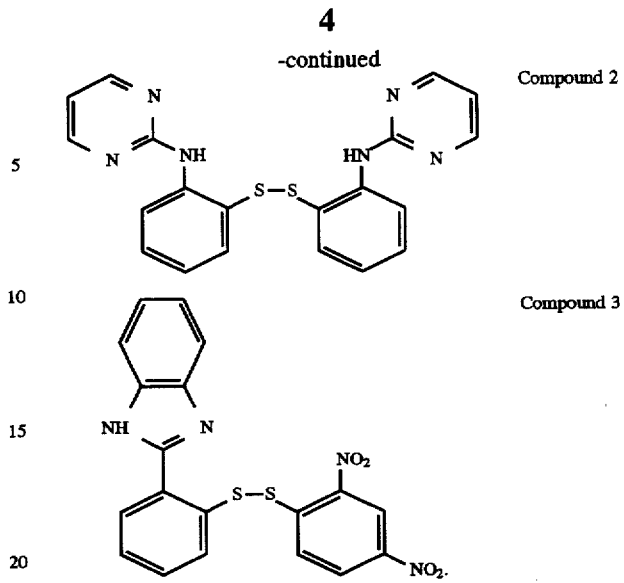

If desired, the diphenyl disulfide compounds of formula (I) may be converted, with pharmacologically acceptable acids, to the corresponding salts which are included within the scope of this invention. Examples of the pharmacologically acceptable acids include a mineral acid such as hydrochloric acid, sulfuric acid, hydrobromic acid and phosphoric acid; an organic sulfonic acid such as methane sulfonic acid, benzenesulfonic acid and p-toluenesulfonic acid; and an organic carboxylic acid such as acetic acid, propionic acid, oxalic acid, succinic acid, maleic acid, fumaric acid, lactic acid, tartaric acid, malic acid and citric acid. This conversion reaction may be performed according to a conventional salt-forming process.

The compounds of the present invention possess a potent activity to inhibit the production of IL-1β, with low toxicity, which are useful for the prophylaxis or therapy of various diseases in which IL-1β would participate, such as, chronic rheumatism, rheumatic polyarthritis, sepsis, systemic lupus erythematosus, systemic scleroderma, Behcet disease, periarteritis nodosa, colitis ulcerosa, active chronic hepatitis, glomerular nephritis, osteoarthritis, gout, atherosclerosis, psoriasis, atopic dermatitis and osteoporosis.

Further, the present diphenyl disulfide compounds possess the activity to inhibit the release of TNFα, which are useful for the prophylaxis or treatment of the diseases wherein TNFα would participate in the pathological progress. Such diseases include acquired immune deficiency syndrome (AIDS) in addition to the diseases in which IL-1β would participate, e.g. chronic rheumatism, rheumatic polyarthritis, sepsis and atopic dermatitis.

A dose of the present compound to exert an effective activity is usually 5 mg to 6 g per adult daily, preferably 10–300 mg. Administration of the present compound include, for example, oral, intravenous, subcutaneous, intramuscular, intrarectal or intra-articular administrations, oral, intra-articular and intravenous administrations being preferable.

The present compounds can be formulated for administration by any conventional methods for forming pharmaceutical preparations.

Examples of preparations include solid preparations such as tablets, granules, powders, hard capsules and soft capsules, and liquid preparations.

The solid preparations may contain any conventional components such as binders, e.g. dextrin, hydroxypropylcellulose, hydroxypropylmethylcellulose, polyvinyl pyrrolidone and macrogol; excipients, e.g. lactose, corn starch, calcium phosphate and magnesium aluminum metasilicate; lubricants, e.g. calcium stearate and talc; disintegrators, e.g. carboxymethyl cellulose and crystalline cellulose. The tablets may be coated by any methods known in the art.

The liquid preparations include aqueous or oily suspensions, emulsions, solutions, syrups, elixirs and others. Alternatively, they may be any dried products capable of being redissolved in water or other suitable vehicle before use. Such liquid preparations may contain any conventional additives such as suspending agents, e.g. sorbitol syrup, carboxymethyl cellulose, gelatin, hydroxyethyl cellulose, aluminium stearate gel and hydrogenated edible oils; emulsifying agents, e.g. lecithin, glycerol monostearate and acasia; non-aqueous vehicles, e.g. palm oil, propylene glycol and ethanol; and antiseptics, e.g. ethyl p-hydroxybenzoate and sorbic acid.

Dosage forms for parenteral administration include injections and suppositories.

Injections may be prepared by a conventional method, if required, by incorporating in the present compounds a pH adjusting agent, a buffer, a stabilizer, a preservative, a solubilizing agent and the like.

This invention is further illustrated by the following examples.

EXAMPLE 1

3.85 g of 2-chloropyrimidine and 6.02 g of 2-aminobenzene disulfide were heated under reflux in ethanol for 18 hours. After the reaction solution was distilled under reduced pressure, the residue was dissolved in chloroform, washed with a 10% aqueous solution of sodium hydroxide and dried over anhydrous sodium sulfate. Purification by silica gel chromatography gave 3.65 g of Compound 1 from the eluate with ethyl acetate/chloroform (1:20) and 2.68 g of Compound 2 from the eluate with ethyl acetate/chloroform (1:10). The physical properties of these compounds are shown in Table 1.

| Compound No. | 1H-NMR, δ | MS |
|---|---|---|
| 1 | 7.18(1H, t, 6Hz), 7.25–7.79(8H, m) 8.65(2H, d, 6Hz), as determined with $CD_3OD$ | 326(M+) |
| 2 | 6.70–6.85(2H, m), 7.20–7.40(2H, m), 8.15(1H, brs), 8.38–8.52(2H, m), as determined with $CDCl_3$ | 404(M+) |

EXAMPLE 2

To a solution of 0.98 g of 2-(2-mercaptophenyl) benzimidazole in pyridine was added 0.72 g of mercury acetate and the mixture was stirred at room temperature for 3 hours. The precipitated crystal was recovered by filtration and dried to give 2-(2-mercaptophenyl)benzimidazole mercuric salt. The crude product was added to acetonitrile and the mixture was cooled with a freezing mixture of sodium chloride and ice. 0.75 g of 2,4-dinitrobenzenesulfenyl chloride was added and stirred under nitrogen atmosphere. After 2 hours, insolubles were recovered by filtration and washed with a mixed solution of chloroform and ethanol.

The filtrate was purified by silica gel chromatography and the eluate with ethyl acetate/chloroform (1:5) was crystallized from chloroform to give 0.22 g of Compound 3. Compound 3 has the following physical properties:

Melting point (°C.): 113.8 IR($cm^{-1}$) (Nujol): 1605, 1540, 1460, 1350 NMR($CDCl_3$, δ): 7.3–7.85(9H,m), 8.18–8.21 (2H,m), 9.04(1H,d,2 Hz)

TEST EXAMPLE 1

Compounds 1–3, the present diphenyl disulfide compounds obtained in Examples 1 and 2, were evaluated for the activity to inhibit the production of IL-1β, in accordance with the following method.

The THP-1 cells derived from human peripheral blood (ATCC TIB202) were suspended in RPMI 1640 medium (available from Bio-Whittaker Co., Ltd.) containing 10% (v/v) of fetal bovine serum, 2 mM of glutamine, 50 μM of 2-mercaptoethanol, 60 μg/ml of penicillin and 100 μg/ml of streptomycin.

The suspension of the THP-1 cell was subcultured at 37° C. under the atmosphere of 95% oxygen and 5% carbon dioxide. A portion of the subcultured suspension was centrifuged at 1200 rpm at room temperature for 3 minutes to recover the subcultured THP-1 cells.

The resulting THP-1 cells were resuspended in RPMI 1640 medium containing 2% (v/v) of fetal bovine serum, 2 mM of glutamine, 50 μM of 2-mercaptoethanol, 60 μg/ml of penicillin and 100 μg/ml of streptomycin so as to provide a final THP-1 cell concentration of $3 \times 10^6$ cells/ml.

The resuspension of the cell was dispensed in 0.5 ml portions to wells of a 24-well plate for cell culture. Then, each solution of the present Compounds 1–3 dissolved in DMSO at the respective specified concentrations was added in 2.5 μl portions to each well. The plate was incubated at 37° C. under the atmosphere of 95% oxygen and 5% carbon dioxide for one hour. Then, 12-o-tetradecanoylphorbol-13-acetate (PMA) and polyinosic acid were added to each well so as to provide final concentrations of 2 μg/ml and 200 respectively. The plate was incubated at 37° C. under the atmosphere of 95% oxygen and 5% carbon dioxide for 24 hours. After incubation, a supernatant was recovered from each well by means of Pipetteman available from Gilson Co., Ltd. Then, an amount of the IL-1β in the supernatant was assayed by means of the enzyme immunoassay kit available from Cayman Chemical Co., Ltd.

The results are summarized below, expressed in terms of $IC_{50}$ values in μM unit, wherein the amount of IL-1β produced at the time of no addition of the dipenyl disulfide compound is defined as 100 and the concentration of each present Compounds 1–3 to inhibit 50% the IL-1β production is defined as $IC_{50}$.

| Test compound | $IC_{50}$ (μM) |
|---|---|
| Compound 1 | 3.8 |
| Compound 2 | 34 |
| Compound 3 | 34 |

TEST EXAMPLE 2

Compound 1, the present diphenyl disulfide compound obtained in Example 1, was evaluated for the activity to inhibit the release of TNFα, in accordance with the following method.

The THP-1 cells derived from human peripheral blood (ATCC TIB202) were suspended in RPMI 1640 medium (available from Bio-Whittaker Co., Ltd.) containing 10% (v/v) of fetal bovine serum, 2 mM of glutamine, 50 μM of 2-mercaptoethanol, 60 μg/ml of penicillin and 100 μg/ml of streptomycin.

The suspension of THP-1 cell was subcultured at 37° C. under the atmosphere of 95% oxygen and 5% carbon dioxide. A portion of the subcultured suspension was centrifuged at 1200 rpm at room temperature for 3 minutes to recover the subcultured THP-1 cells.

The resulting THP-1 cells were resuspended in RPMI 1640 medium containing 2% (v/v) of fetal bovine serum, 2 mM of glutamine, 50 µM of 2-mercaptoethanol, 60 µg/ml of penicillin and 100 µg/ml of streptomycin so as to provide a final THP-1 cell concentration of $3 \times 10^6$ cells/ml.

The resuspension of the cell was dispensed in 0.5 ml portions to wells of a 24-well plate for cell culture, and incubated at 37° C. for one hour. Each solution of the present Compound 1 dissolved in DMSO at the respective specified concentrations was added in 2.5 µl portions to each well. The plate was incubated at 37° C. under the atmosphere of 95% oxygen and 5% carbon dioxide for one hour. Then, PMA and polyinosic acid were added to each well so as to provide final concentrations of 2 µg/ml and 200 µg/ml, respectively. The plate was incubated at 37° C. under the atmosphere of 95% oxygen and 5% carbon dioxide for 24 hours. After incubation, a supernatant was recovered from each well by means of Pipetteman available from Gilson Co., Ltd. An amount of TNFα in the supernatant was assayed by means of the human TNFα ELISA kit available from Genzyme Co., Ltd.

The results are summarized below, expressed in terms of $IC_{50}$ values in µM unit, wherein the amount of TNFα released at the time of no addition of the dipenyl disulfide compound is defined as 100 and the concentration of the present Compound 1 to inhibit 50% the TNFα release is defined as $IC_{50}$.

| Test Compound | $IC_{50}$ (µM) |
|---|---|
| Compound 1 | 19 |

TEST EXAMPLE 3

Compounds 1–3, the present diphenyl disulfide compounds obtained in Examples 1 and 2, were evaluated for the cytotoxicity, in accordance with the following method.

The THP-1 cells derived from human peripheral blood (ATCC TIB202) were suspended in RPMI 1640 medium (available from Bio-Whittaker Co., Ltd.) containing 10% (v/v) of fetal bovine serum, 2 mM of glutamine, 50 µM of 2-mercaptoethanol, 60 µg/ml of penicillin and 100 µg/ml of streptomycin.

The suspension of THP-1 cell was subcultured at 37° C. under the atmosphere of 95% oxygen and 5% carbon dioxide. A portion of the subcultured suspension was centrifuged at 1200 rpm at room temperature for 3 minutes to recover the subcultured THP-1 cells. The resulting THP-1 cells were resuspended in RPMI 1640 medium containing 2% (v/v) of fetal bovine serum, 2 mM of glutamine, 50 µM of 2-mercaptoethanol, 60 µg/ml of penicillin and 100 µg/ml of streptomycin so as to provide a final THP-1 cell concentration of $1 \times 10^6$ cells/ml.

The resuspension of the cell was dispensed in 1 ml portions to wells of a 24-well plate for cell culture. Then, each solution of the present Compounds 1–3 dissolved in DMSO at the respective specified concentrations was added in 5 µl portions to each well. The plate was incubated at 37° C. under the atmosphere of 95% oxygen and 5% carbon dioxide for 24 hours. After incubation, 100 µl of Alamar Blue (available from Biosource Co., Ltd.) was added to each well and then incubation was further continued at 37° C. under the atmosphere of 95% oxygen and 5% carbon dioxide for 3 hours.

After incubation, a supernatant was recovered by means of the Pipetteman available from Gilson Co., Ltd. and determined for a difference in absorbances at 570 nm and 600 nm. The difference in absorbances at 570 nm and 600 nm for the test solution containing no diphenyl disulfide compound was used as a standard. If the difference in absorbance is significantly reduced upon the addition of Compounds 1–3 of the present invention, it is estimated that there is cytotoxicity.

The above test demonstrated that no cytotoxicity was found in Compounds 1–3 at the concentration up to 50 µM.

PREPARATION EXAMPLE 1

Tablets were prepared using the following formulation per tablet.

| Tablets | |
|---|---|
| Compound 1 | 20 mg |
| Magnesium silicate | 20 mg |
| Lactose | 98.5 mg |
| Hydroxypropylcellulose | 7.5 mg |
| Magnesium stearate | 1 mg |
| Vegetable hardened oil | 3 mg |

Compound 1, magnesium silicate and lactose were blended and kneaded with an alcoholic solution containing hydroxypropylcellulose. The resulting mixture was granulated to a suitable particle size, dried and sized. Then, magnesium stearate and vegetable hardened oil were blended to form uniform granules and then the granules were formed to tablets by means of a rotary tableting machine, each tablet having a diameter of 7.0 mm, a weight of 150 mg and a hardness of 6 kg.

PREPARATION EXAMPLE 2

| Granules | |
|---|---|
| Compound 1 | 10 mg |
| Magnesium oxide | 40 mg |
| Calcium hydrogenphosphate | 38 mg |
| Lactose | 10 mg |
| Hydroxypropylcellulose | 20 mg |

All the above components except for hydroxypropylcellulose were blended and then an alcoholic solution containing hydroxypropylcellulose was added and kneaded. The resulting mixture was granulated by means of an extrusion granulating machine and dried to form granules, which were then sized and passed through a 12 mesh sieve. The product left on a 48 mesh sieve was obtained as granules.

PREPARATION EXAMPLE 3

| Syrups | |
| --- | --- |
| Compound 1 | 1.000 g |
| Sucrose | 30.000 g |
| 70 w/v % D-Sorbitol | 25.000 g |
| Ethyl p-hydroxybenzoate | 0.030 g |
| Propyl p-hydroxybenzoate | 0.015 g |
| Flavoring agent | 0.200 g |
| Glycerol | 0.150 g |
| 96% Ethanol | 0.500 g |
| Purified water | ad lib. |
| Total | 100 ml |

Sucrose, D-sorbitol, ethyl p-hydroxybenzoate, propyl p-hydroxybenzoate and Compound 1 were dissolved in 60 g of purified water (warm water). After cooling, a solution of the flavoring agent in glycerol and 96% ethanol was added. To the resulting mixture was added purified water to make it up to 100 ml.

PREPARATION EXAMPLE 4

| Injections | |
| --- | --- |
| Hydrochloride of Compound 1 | 10.0 mg |
| Sodium chloride | 81.0 mg |
| Sodium bicarbonate | 8.40 mg |
| Distilled water for injection | ad lib. |
| Total | 10.0 ml |

Sodium bicarbonate, sodium chloride and hydrochloride of Compound 1 were dissolved in distilled water for injection to make up injections, each having a total volume of 10.0 ml.

PREPARATION EXAMPLE 5

| Suppositories | |
| --- | --- |
| Compound 1 | 2 g |
| Macrogol (Polyethylene glycol) 4000 | 20 g |
| Glycerol | 78 g |
| Total | 100 g |

Compound 1 was dissolved in glycerol and then Macrogol 4000 was added. The mixture was dissolved under heat, poured into a suppository mold and then solidified by cooling to form suppositories, each weighing 1.5 g.

What is claimed is:

1. A compound, having the formula

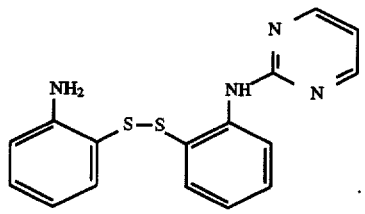

2. A compound, having the formula

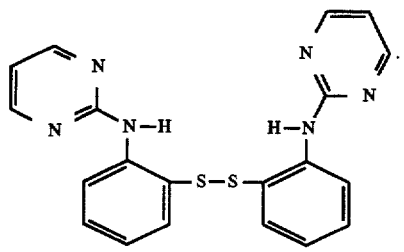

3. A compound, having the formula

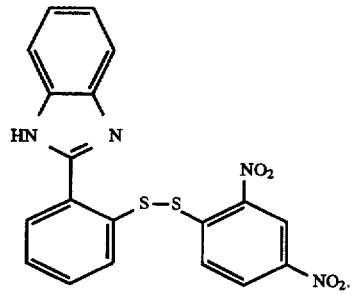

4. A pharmaceutical composition which comprises as an active ingredient a compound of claim 1 or the pharmacologically acceptable salt thereof and a pharmaceutically acceptable carrier.

5. A pharmaceutical composition which comprises as an active ingredient a compound of claim 2 or the pharmacologically acceptable salt thereof and a pharmaceutically acceptable carrier.

6. A pharmaceutical composition which comprises as an active ingredient compound of claim 3 or the pharmacologically acceptable salt thereof and a pharmaceutically acceptable carrier.

* * * * *

UNITED STATES PATENT AND TRADEMARK OFFICE
CERTIFICATE OF CORRECTION

PATENT NO. : 5,698,564
DATED : December 16, 1997
INVENTOR(S) : Koichi KATSUYAMA et al.

It is certified that error appears in the above-identified patent and that said Letters Patent is hereby corrected as shown below:

On the title page, Item[30], the Foreign Application Date should read:

-- Dec. 26, 1994 --

Signed and Sealed this

Twenty-fourth Day of February, 1998

Attest:

BRUCE LEHMAN

*Attesting Officer*     *Commissioner of Patents and Trademarks*